United States Patent [19]

Stache et al.

[11] Patent Number: 4,762,648

[45] Date of Patent: Aug. 9, 1988

[54] MONOFUNCTIONAL AND BISFUNCTIONAL ANTHRAQUINONE-(OXY-2,3-OXIDOPROPANES), PROCESSES FOR THEIR PREPARATION, AND THEIR USE AS DRUGS

[75] Inventors: Ulrich Stache, Hofheim am Taunus; Hans P. Kraemer; Hans-Harald Sedlacek, both of Marburg, all of Fed. Rep. of Germany

[73] Assignee: Hoechst Aktiengesellschaft, Marburg, Fed. Rep. of Germany

[21] Appl. No.: 645,266

[22] Filed: Aug. 29, 1984

[30] Foreign Application Priority Data

Aug. 31, 1983 [DE] Fed. Rep. of Germany ....... 3331296

[51] Int. Cl.$^4$ .................. C07C 50/34; C07D 303/12
[52] U.S. Cl. ................................ 260/383; 260/376; 260/384; 549/512; 549/543; 549/544; 549/555
[58] Field of Search ............... 260/383, 376, 384; 549/555, 544, 543, 512, 556; 514/680

[56] References Cited

U.S. PATENT DOCUMENTS

| | | | |
|---|---|---|---|
| 3,096,349 | 7/1963 | Meyer et al. | 549/555 |
| 4,111,907 | 9/1978 | Green et al. | 549/555 |
| 4,304,724 | 12/1981 | Nutt | 260/369 |
| 4,657,842 | 4/1987 | Finter et al. | 522/48 |

OTHER PUBLICATIONS

J. Zaagsma and W. Th. Nauta; J. Med. Chem. 17 (1974), 507–513.
Barton and Ollis, Comprehensive Organic Chemistry (vol. 1), pp. 1213 and 1216 (Pergamon Press 1979).
Budziarek, Chemical Abstracts, 90:87118z (1979).
Bell et al., Chemical Abstracts, 90:87121v (1979).
Chen, Chemical Abstracts, 93:151542z (1980).
Stapleton and Waters, Chemical Abstracts, 95:26492y (1981).
Cambie et al., Chemical Abstracts, 95:150252j (1981).
Cambie et al., Chemical Abstracts, 96:5890g (1982).
Popov and Volosenko, Chemical Abstracts, 97:38637d (1982).
Seguchi and Ozasa, Chemical Abstracts, 98:71620m (1983).
Boddy et al., Chemical Abstracts, 98:88942r (1983).
Fieser and Fieser, Organische Chemie, (2nd Ed. 1982), pp. 1368–1379 (Weinheim 1982).

*Primary Examiner*—Glennon H. Hollrah
*Assistant Examiner*—Raymond Covington
*Attorney, Agent, or Firm*—Finnegan, Henderson, Farabow, Garrett and Dunner

[57] ABSTRACT

The present invention relates to a novel mono-functional and bis-functional anthraquinone-(oxy-2,3-oxidopropanes) and to a process for their preparation. The compounds according to the invention are useful as intermediates in the preparation of drugs possessing a $\beta$-receptor blocker action and as crosslinking agents in the preparation of polymers, and moreover exhibit cytostatic activity.

6 Claims, No Drawings

MONOFUNCTIONAL AND BISFUNCTIONAL ANTHRAQUINONE-(OXY-2,3-OXIDOPROPANES), PROCESSES FOR THEIR PREPARATION, AND THEIR USE AS DRUGS

The present invention relates to novel monofunctional and bisfunctional anthraquinone-(oxy-2,3-oxidopropanes) of the formula I

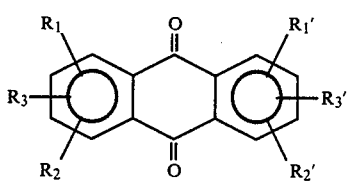

where $R_1$ and $R_1'$ are identical or different and are hydrogen, hydroxyl or the radical

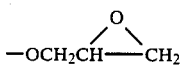

$R_2$ and $R_2'$ are identical or different and are hydrogen or one or more hydroxyl, $C_1$-$C_4$-alkyl, $C_1$-$C_4$-alkoxy, $C_1$-$C_4$-alkoxycarbonyl, $C_1$-$C_4$-alkanoyloxy, aryloxy, Ar—$C_1$-$C_4$-alkyloxy, halogen or nitro groups, and $R_3$ and $R_3'$ are identical or different and are hydrogen or the radical

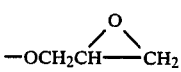

The invention moreover relates to a process for the preparation of compounds of the formula I, wherein a mono- or di- or poly-hydroxyanthraquinone of the formula II

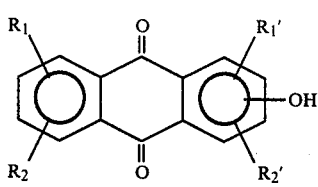

(the OH group shown being in position 1, 2, 3, 4, 5, 6, 7 or 8)

where $R_1$ and $R_1'$ are H and/or OH and $R_2$ and $R_2'$ have the above meanings, is either 1. reacted with epichlorohydrin or epibromohydrin in the presence of a base, if appropriate with addition of an inert organic solvent, at temperatures from 0° C. to the boiling point of the particular reaction mixture, to give the compound according to the invention, of the formula I, or 2. is reacted with epichlorohydrin or epibromohydrin in the presence of a base, if appropriate with addition of an inert organic solvent, at temperatures from 0° C. to the boiling point of the particular reaction mixture, to give a compound of the formula III

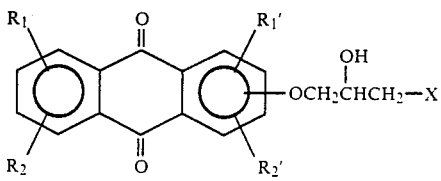

X = Hal = F, Cl, Br or I OH where $R_1$ and $R_1'$ is H, OH or

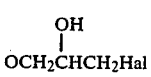

and $R_2$ and $R_2'$ have the above meaning, and this is converted to the compound according to the invention, of the formula I, by treatment with an inorganic or organic base, if appropriate with addition of an inert organic solvent and/or water, HalH being eliminated, or 3. (a) is reacted with a glycidol of the formula IV $$H_2C \underset{\diagdown O \diagup}{-} CHCH_2OR_4 \quad \text{IV}$$

where $R_4$ is H, alkyl, acyl or an alkylsulfonic or arylsulfonic acid ester, preferably H, if appropriate with addition of a base and of an inert organic solvent, with or without addition of water, to give a compound of the formula V

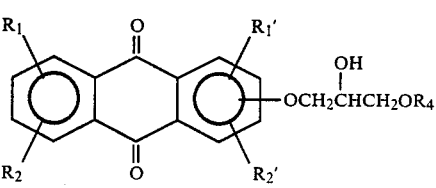

where $R_1$ and $R_1'$ is H, OH or

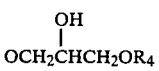

and $R_2$ and $R_2'$, as well as $R_4$, have the above meanings, and the compound of the formula V, if $R_4$ is alkyl or preferably acyl, is hydrolized to give a compound of the general formula V where $R_4$=H, and this latter compound is converted, by reaction with an alkylsulfonic or arylsulfonic acid halide, to a compound of the formula V in which $R_4$ is an alkylsulfonic or arylsulfonic acid radical, and this compound, where appropriate after nucleophilic replacement of the alkylsulfonic or arylsulfonic acid ester group $R_4$ by halogen, such as F, Cl, Br or I, is converted by treatment with a base—unless the elimination takes place even without such added base—to the compound according to the invention, of the formula I, by elimination of alkylsulfonic or arylsulfonic acid or of hydrogen halide if $R_4$ is F, Cl, Br or I, or (b) is reacted with a 1-halogen-2,3-dihydroxypropane or 1-alkyl- or 1-aryl-sulfonato-2,3-dihydroxypropane of the formula VI

R₅CH₂CHOHCH₂OH,         VI where R₅ is chlorine, bromine, iodine or an alkylsulfonic or arylsulfonic acid ester radical, and a base, preferably a strong inorganic alkali, where appropriate with addition of an inert organic solvent, to give a compound of the formula VII

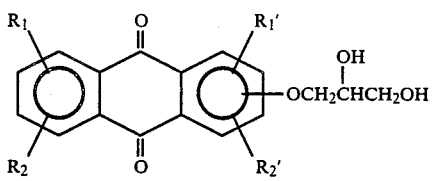

where R₁ and R₁' are H, OH or OCH₂CH(OH)CH₂OH and R₂ and R₂' have the above meaning, and this compound is then converted further, in accordance with 3.(a), to give the compound of the formula I or (c) is reacted with a derivative of 1-halogeno- or 1-alkyl- or 1-aryl-sulfonato-2,3-dihydroxypropane of the formula VIII

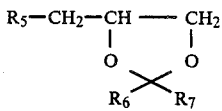

where R₅ has the above meaning and R₆ and R₇ individually or jointly are H, alkyl, phenyl or benzyl, in the presence of a base, preferably a strong inorganic alkyl, if appropriate with addition of an inert organic solvent to give a compound of the formula IX

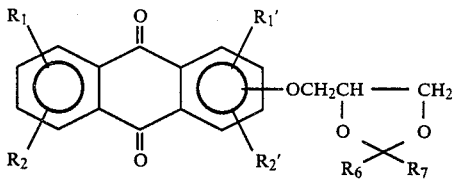

where R₁ and R₁' are H, OH or

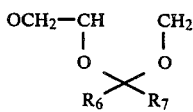

and R₂, R₆ and R₇ have the above meanings, this compound is then converted by acid hydrolysis to a compound of the formula VII and the latter is then further converted in accordance with 3.(a) to the compound according to the invention, of the formula I, or 4. is reacted with an alkyl chloride, bromide or iodide in the presence of a base, where appropriate with addition of an inert organic solvent, at temperatures from 0° C. to the boiling point of the particular reaction mixture, to give a compound of the formula X

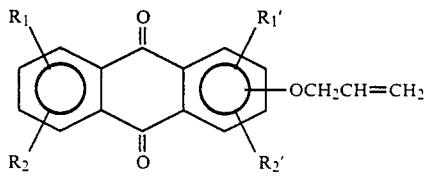

where R₁ and R₁' are H, OH or OCH₂CH=CH₂ and R₂ and R₂' have the above meanings, and this compound is then converted by means of an organic alkylpercarboxylic acid or arylpercarboxylic acid in an inert organic solvent, or by means of the (I₂.AgO) complex to a compound according to the invention of the formula I.

To convert the mono- or di- or poly-hydroxyanthraquinones of the formula II to monofunctional and bisfunctional anthraquinone-(oxy-2,3-oxidopropanes) of the formula, the following procedure is employed:

PROCESS VARIANT 1

(Formula II→Formula I)

Suitable bases for the reaction are, preferably, inorganic bases, especially sodium hydroxide, potassium hydroxide, sodium and potassium methylate, ethylate or tert.-butylate and sodium, potassium and calcium carbonates or bicarbonates. DEWEX-1 (in the OH form) can be used in place of a base. Preferred inert solvents to use are acetone, methyl ethyl ketone, dimethylformamide, acetonitrile, HMPT or alcohols, for example tert.-butanol. The reaction should preferably be carried out between 0° C. and the boiling point of the solvent used. Water formed during the etherification process is preferably removed via a reverse water separator. This is especially the case if the reaction is carried out exclusively in epichlorohydrin or epibromohydrin without further added solvent. A gentle and advantageous variant of the process comprises boiling the reaction mixture, for from 1 to 480 hours in the presence of the potassium carbonate, to bind the hydrogen halides, in methyl ethyl ketone. In this variant, if epichlorohydrin and dihydroxyantraquinones are used and the mixture is boiled briefly, for example up to 48 hours but also for longer, as a rule substantially selectively only one of the two hydroxyl groups is converted to the glycidyl ether, while to react the second hydroxyl group the reaction time must be increased substantially to as much as 500 hours or even more. However, the bifunctional conversion of the dihydroxyanthraquinones into their bisglycidyl ethers takes place, surprisingly, with substantially better yields (about 60%), and also in a shorter reaction time, with the more reactive epibromohydrin than with epichlorohydrin. Moreover, the reaction with epibromohydrin also takes place more completely to give oxy-2,3-oxidopropane groups than in the case of epichlorohydrin, i.e. less of the primary product of the formula III, if any at all, is obtained. If, however, primary product III is found in the reaction product, mixed with I, it is completely converted to the title product I by further refluxing in an organic solvent in the presence of an alkali, or by treatment with triethylamine in tetrahydrofuran, hydrogen chloride or hydrogen bromide being eliminated. Purification of the process products obtained can also be effected by recrystallization or by conventional chromatography on aluminum oxide or silica gel. Separation of the reaction products in a reaction mixture, for example of the monoglycidyl ether and diglycidyl ether of a dihydroxyanthraquinone or polyhydroxyanthraquinone, is advantageously carried out by chromatography. To monitor the course of the reactions, thin layer chromatography is used. This unambiguously reveals the course and degree of selectivity of the reactions, especially when dihydroxyanthraquinones are used. The Rf values of monoglycidyl ethers and diglycidyl ethers of a particular dihydroxyanthraquinone or polyhydroxyanthraquinone employed are as a rule far apart. Thin layer chromatography control of the reaction course proves particularly advantageous in the preparation of hydroxyanthraquinone-oxy-2,3-oxidopropanes, since in that case the reaction has to be stopped in good time, before it proceeds to the anthraquinone-di-(oxy-2,3-oxidopropanes). However, monitoring the course of the reaction by thin layer chromatography has also proved very valuable in monitoring the formation of anthraquinone-di-(oxy-2,3-oxidopropanes).

The practical conditions for carrying out the reaction, described above, as a rule also apply to analogous ether formation reactions effected by bases or alkalis, as explained in the following process variants.

PROCESS VARIANT 2

(Formula II→III→I)

Brief heating—for about 1 to 12 hours—of monohydroxyanthraquinones or dihydroxyanthraquinones according to process variant 1 with epichlorohydrin and epibromohydrin results in preferred formation of the halogenohydrins of the formula III. Moreover, these are also obtained in good yield if the monohydroxyanthraquinones or dihydroxyanthraquinones are boiled under reflux with 1 to 3 moles, preferably 1.1 to 1.4 moles, of epibromohydrin or preferably epichlorohydrin in the presence of catalytic amounts of piperidine for from 1 to 16 hours, preferably for 6–8 hours. Subsequent treatment of the compounds of the formula III with alkalis, preferably with normal sodium hydroxide solution in tetrahydrofuran, at 30°–70° C. for 1–3 hours, gives the compounds of the formula I by elimination of hydrogen halide.

PROCESS VARIANT 3

(II+IV→V→I)

The reaction of the anthraquinones II with glycidol IV or its derivatives ($R_4$ in IV=$CH_3$, $COCH_3$, $SO_2CH_3$ etc.) is carried out under the same conditions as described for the reaction with epichlorohydrin or epibromohydrin under process variant 1. Here again, thin layer chromatography is employed to monitor the progress of the reaction. For further conversion of V into I, V ($R_4$=H) is preferably reacted with methanesulfonic acid chloride or p-toluenesulfonic acid chloride in dioxane/pyridine at 0° C. to 20° C. to give the corresponding sulfonic acid ester derivatives (V: $R_4$=$SO_2CH_3$, $SO_2C_6H_4$-p-$CH_3$) and these are thereafter reacted directly, or after nucleophilic conversion, with an alkali metal bromide or iodide, preferably in dimethylformamide, if appropriate with addition of an alkali metal carbonate, to give the corresponding halides (V: $R_4$=Br or I) which are then converted, by boiling with alkalis, preferably in alcohols or acetone or butan-2-one, or by treatment with tertiary organic bases, preferably triethylamine, in ethers, for example tetrahydrofuran or dioxane or dimethoxy-glycol, or in xylene, so as to form an epoxide group and give the title compounds of the formula I.

PROCESS VARIANT 4

(II→VII→I)

The hydroxyanthraquinones II are boiled under reflux with 1-chloro-, 1-bromo- or 1-iodo-propane-2,3-diol, preferably in alcohols or dimethylformamide or dimethoxyethane, and with an alkali, preferably an alkali metal alcoholate, until the reaction is complete. The further reactions to give I are carried out analogously to those described in process variant 3.

PROCESS VARIANT 5

(II→VIII→VII→I)

The hydroxyanthraquinones II are reacted, preferably with 1-bromo-1-iodo- or 1-(p-toluenesulfonato)-propane-2,3-diol-2,3-acetonide, analogously to what has been described for the free 1-halogen-propane-2,3-diols in process variant 4, to give compounds of the formula VIII, and these are subsequently hydrolyzed by treatment with mineral acids, preferably hydrochloric acid or sulfuric acid, in a alcohol or acetone/water mixture, to give compounds of the formula VII. The reaction to give the title compounds I is carried out analogously to process variant 4 or 3.

PROCESS VARIANT 6

(II→X→I)

The conversion of hydroxyanthraquinones to the mono- or di-allyloxyanthraquinones X is carried out analogously to the conversion of I→II described under procedure 1. Instead of epichlorohydrin or epibromohydrin, allyl chloride, allyl bromide or allyl iodide are preferably used.

To convert X into I, the anthraquinone allyl ethers X are reacted with appropriate molar equivalents of an organic alkyl- or aryl-percarboxylic acid, preferably with m-chloroperbenzoic acid, in an inert organic solvent, preferably methylene chloride, chloroform or ethyl acetate, at 0° C.-40° C., during which reaction m-chlorobenzoic acid as a rule precipitates, and is filtered off. The compounds according to the invention, of the formula I, can then be isolated from the filtrate by concentration and recrystallization.

In an alternative variant, the process products I can be obtained from the anthraquinone allyl ethers by reaction with the iodine/silver oxide oxidation complex ($I_2 \times Ag_2O$) in water/dioxane.

The selective reactivity, leading to the products according to the invention, must be regarded as surprising.

The following hydroxyanthraquinones, which as a rule are known from the literature, are suitable starting compounds for the preparation of the anthraquinone-mono- or -bis-(oxy-2,3-oxido-propanes) I: 1- or 2-hydroxyanthraquinones; 1,5-, 1,6-, 1,7-, 1,8-, 2,6- and 2,7-, 1,2-, 1,3-, 1,4- and 2,4-dihydroxyanthraquinone, and trihydroxy-anthraquinones and tetrahydroxyanthraquinones, which anthraquinones can additionally contain one or more identical or different substituents, which are preferably halogen, alkyl, alkoxy, acyloxy or nitro.

The following glycidyl ethers are obtained as process products according to the invention from the anthraquinone starting materials: anthraquinone-1-oxy-(2,3- oxidopropane), anthraquinone-2-oxy-(2,3-oxido-propane), 1-hydroxyanthraquinone-5-oxy-(2,3-oxido-propane), 5-hydroxyanthraquinone-1-oxy-(2,3-oxido-propane), 1-hydroxyanthraquinone-6-oxy-(2,3-oxido-propane), 6-hydroxyanthraquinone-1-oxy-(2,3-oxido-propane), 1-hydroxyanthraquinone-7-oxy-(2,3-oxido-propane), 7-hydroxyanthraquinone-1-oxy-(2,3-oxido-propane), 1-hydroxyanthraquinone-8-oxy-(2,3-oxido-propane), 8-hydroxyanthraquinone-1-oxy-(2,3-oxido-propane), 2-hydroxyanthraquinone-6-oxy-(2,3-oxido-propane), 6-hydroxyanthraquinone-2-oxy-(2,3-oxido-propane), 2-hydroxyanthraquinone-7-oxy-(2,3-oxido-propane), 7-hydroxyanthraquinone-2-oxy-(2,3-oxido-propane), anthraquinone-1,5-bis-(oxy-2,3-oxido-propane), anthraquinone-1,6-bis-(oxy-2,3-oxido-propane), anthraquinone-1,7-bis-(oxy-2,3-oxido-propane), anthraquinone-1,8-bis-(oxy-2,3-oxido-propane), anthraquinone-2,6-bis-(oxy-2,3-oxido-propane), anthraquinone-2,7-bis-(oxy-2,3-oxido-propane), anthraquinone-1,2-bis-(oxy-2,3-oxido-propane), anthraquinone-1,3-bis-(oxy-2,3-oxido-propane), anthraquinone-1,4-bis-(oxy-2,3-oxido-propane) and anthraquinone-2,3-bis-(oxy-2,3-oxido-propane), which products may additionally contain one or more identical or different substituents which preferably are halogen, alkyl, alkoxy, hydroxy, acyloxy or nitro.

The products obtainable according to the invention are valuable intermediates for the preparation of cardiovascular agents of the structural type of the β-receptor blockers. Moreover, the anthraquinone-bis-(oxy-2,3-oxido-propanes) can be employed as novel, previously unknown, crosslinking agents in the preparation of polymers, for example epoxy resins and surface coatings, in the plastics and surface coatings sector.

In addition, the products surprisingly show, in various in vitro and in vivo test models, an anti-tumoral activity comparable to and often even superior to that of adriamycin. The acute toxicity of the compounds according to the invention is at the same time significantly lower than that of the comparison standard adriamycin, i.e. the products show a higher therapeutic index than adriamycin. The various test systems for assaying the in vitro and in vivo anti-tumoral action and the acute toxicity are described in the section which follows.

(a) Determination of the cytotoxic activity in vitro

The determination of the cytotoxic activity of the compounds described in the present patent is carried out on L 1210 leukemia cells of the mouse. Specifically, the following test systems were used:

PROLIFERATION ASSAY

In this in vitro method, after incubation of the cells with varying concentrations of the test substance a determination is carried out of the extent to which the cells can incorporate radioactively labelled DNA-precursors (for example C-14-labelled thymidine).

L 1210 Cells in the exponential growth phase ($5 \times 10^3$/ml in RPMI 1640) are incubated for 72 hours, in a microtitration plate, with different concentrations of the test substance (37° C., 5% $CO_2$, 95% relative atmospheric humidity). Controls consist of cells which are incubated solely with fresh medium. All assays are carried out in quadruplicate. After 65 hours, 50 μl of C-14-thymidine (1.5 μc/ml) are added in order to radioactively label the DNA of the cell. After 7 hours' incubation, the cells are filtered off with suction, and the DNA is precipitated with 5% strength dichloroacetic acid and successively washed with water and methanol. After drying at 50° C., the radioactivity built into the DNA is determined after adding 5 ml of scintillation fluid.

The results are quoted as a ratio of the scintillation indices obtained after incubation with the test substance and obtained with the untreated control. From the measurements thus obtained, the dose/effect curve is determined and the $IC_{50}$, i.e. the concentration which under test conditions reduces the incorporation of radioactive thymidine by 50% relative to the control, is determined graphically. The $IC_{50}$ values of the compounds described in this patent, compared to that of adriamycin (ADM), are summarized in Table 1.

(b) Colony formation of L 1210 leukemia cells in soft agar

This method is used to demonstrate an effect of the test substances on the growth characteristics of the cells over several generations (with a cell cycle time of 10–12 hours, about 14 successive generations are observed over the test period of 7 days). In this test, cytostatically active substances produce a reduction of the number of colonies observed relative to an untreated control. Specifically, the test is carried out as follows:

500 Leukemia cells per plate are incubated with different concentrations of test substance for 1 hour at 37° C. The cells are then washed twice with McCoy 5a medium and finally, after addition of 0.3% of agar, poured out into Petri dishes. Controls are incubated with fresh medium only. In place of the 1-hour incubation, different concentrations of the test substance are in some cases mixed into the upper agar layer so as to achieve continuous exposure of the cells over the entire incubation period. After the agar has solidified, the plates are incubated in an incubating chamber for 7 days at 37° C. (5% $CO_2$, 95% relative atmospheric humidity). Thereafter, the number of colonies formed which have a diameter of 60μ is counted. The results are quoted as the number of colonies in the treated agar plates expressed as a percentage of those in the untreated control. From the dose/effect curve thus obtained, the $IC_{50}$ is determined and serves as a measure of the effectiveness of the substance. The results for the compounds described here, compared to adriamycin, are summarized in Table 1.

Table 1 shows that the products surprisingly exert, under in vitro conditions, an anti-tumoral activity against L 1210 leukemia cells in the mouse which is comparable with that of adriamycin or, depending on the structure, is often even superior.

DETERMINATION OF ACUTE TOXICITY

To determine the acute toxicity, NMRI mice were injected intraperitoneally, on day 0, with different doses of the test substance suspended in 0.5 ml of 0.5% strength carboxymethylcellulose. Control groups were given solely 0.5 ml of carboxymethylcellulose solution. 5 Mice were employed per concentration of test substance. On day 14, the number of surviving mice is determined and the $LD_{50}$ found therefrom by the Litchfield Wilcoxon method. The toxicity of the compounds described in this patent, compared to that of adriamycin, is summarized in Table 1.

TABLE 1

| Substance | Proliferation assay IC$_{50}$ ($\mu$g/ml) | Stem cell assay IC$_{50}$ ($\mu$g/ml) Incubation: | | Acute toxicity (mg/kg) LD$_{50}$ |
|---|---|---|---|---|
| | | Continuous | 1 hour | |
| Adriamycin | $6 \times 10^{-3}$ | $2 \times 10^{-2}$ | $4.4 \times 10^{-2}$ | 14 |
| Example 5 | $4.4 \times 10^{-3}$ | $1 \times 10^{-2}$ | $8.3 \times 10^{-3}$ | 200 |
| Example 4 | $2.2 \times 10^{-3}$ | $3.3 \times 10^{-3}$ | $4 \times 10^{-3}$ | |
| Example 3 | $2.8 \times 10^{-2}$ | $3 \times 10^{-2}$ | $6.6 \times 10^{-2}$ | |
| Example 8 | $2.8 \times 10^{-2}$ | $8.5 \times 10^{-3}$ | $3 \times 10^{-2}$ | |

DESCRIPTION OF EXPERIMENTS

Melting point: Tottoli apparatus (from Büchi), uncorrected. IR-spectrum (in KBr): Perkin-Elmer 521 grating spectrophotometer. In each case only characteristic bands are listed. UV spectra (in methanol): Beckman DK 1A spectrophotometer. $^1$H-NMR spectra (unless otherwise mentioned), in CDCl$_3$ (with tetramethylsilane as internal standard): Varian A 60 or T 60. Mass spectra (MS): MS 9 apparatus (from AEI). Thin layer chromatography (TLC): prepared silica gel plates F 254 (from Merck). The mobile phase used was, unless stated otherwise, a 4:1 CH$_2$Cl$_2$/ethyl acetate mixture (migration distance 15 cm; developed once). If identification by the intrinsic color of the anthraquinone compounds was not exact, the spots were rendered visible by irradiation with ultraviolet light. Column chromatography was carried out, unless stated otherwise, with aluminum oxide from Woelm, neutral, activity level II. Because of the sensitivity of the epoxide groups, strictly acid-free methylene chloride was always used.

EXAMPLE 1

Anthraquinone-2-(oxy-2,3-oxido-propane)

a. A solution of 3 g of sodium hydroxide in 7 ml of water is added dropwise, over 30 minutes, with vigorous stirring, to a solution or suspension of 10 g of 2-hydroxy-anthraquinone in 100 ml of epichlorohydrin, boiling vigorously under a water separator (bath temperature about 150°). The mixture is then heated for a further 8 hours so as to boil briskly under the water separator, with vigorous stirring. The precipitated sodium chloride is filtered off with suction. The filter residue is washed with about 100 ml of acid-free methylene chloride. The combined filtrates are initially freed from solvent and excess epichlorohydrin under slightly reduced pressure (80–100 mm Hg). The distillation residue is then dissolved in methylene chloride and filtered through an aluminum oxide column (h=10 cm, 0=3 cm), using about 500 ml of mehtylene chloride as the eluant. After the solvent has been distilled off, the residue is recrystallized from methylene chloride/methanol, with addition of diethyl ether to ensure that it crystallizes out completely. 4.2 g of anthraquinone-2-(oxy-2,3-oxido-propane) of melting point 194°–197° C. are obtained.

Mass spectrum: m/e=280 (M+).

1H-NMR spectrum (in DMSO): Characteristic signal pattern for the

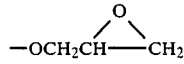

group: $\delta$=2.8 ppm (AB part of an ABX-spectrum, C$\underline{H}_2$—1); $\delta$=3.4 ppm (m, C$\underline{H}$—2); $\delta$=4.3 ppm (AB part of an ABX-spectrum, C$\underline{H}_2$—3).

IR spectrum: Bands at 3080, 1675, 1590, 1580, 1500, 1330, 1300, 1240, 1150, 1030, 935 850, 775, 715 cm$^{-1}$.

TLC (migrating agent CH$_2$Cl$_2$; CH$_3$OH=19:1); R$_F$=0.6 (Starting material: R$_F$=0.8).

b. 21.9 ml of epibromohydrin and 29 ml of 1N aqueous sodium hydroxide solution are added to 3.5 g of 2-hydroxyanthraquinone in 29 ml of dioxane and the mixture is stirred for 2.5 hours at 50° C. It is concentrated and the residue is repeatedly extracted with methylene chloride. After further treatment and isolation of the substance, analogously to the description given in Example 1a., 1.2 g of anthraquinone-2-(oxy-2,3-oxido-propane), having the same physical and spectral data as given in Example 1a., are obtained.

EXAMPLE 2

Anthraquinone-1-(oxy-2,3-oxido-propane)

27 g of potassium carbonate and 135 ml of epibromohydrin are added to a solution of 27 g of 1-hydroxyanthraquinone in 630 ml of methyl ethyl ketone and the batch is heated under reflux for 100 hours, with stirring. It is then filtered through a filter having a layer of clarifying agent, the filtrate is concentrated in vacuo and the residue is recrystallized from methyl ethyl ketone with addition of sufficient methylene chloride to cause complete dissolution. 13.5 g of anthraquinone-1-(oxy-2,3-oxido-propane) of melting point 177°–180° C. are obtained.

Mass spectrum: m/e=280 (M+).

1H-NMR spectrum:

Characteristic signal pattern for

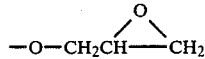

group: $\delta$=3.0 ppm (AB part of an ABX-spectrum, C$\underline{H}_2$—3); $\delta$=3.45 ppm (m, C$\underline{H}$—2); $\delta$=4.3 ppm (AB part of an ABX-spectrum, C$\underline{H}_2$—1).

The pattern of aromatic bands is located between 7.25 and 8.3 ppm.

EXAMPLE 3

1-Hydroxy-anthraquinone-4-(oxy-2,3-oxido-propane)

a. 20.5 g of potassium carbonate and 100 ml of epichlorohydrin are added to a solution of 20 g of 1,4-dihydroxyanthraquinone in 500 ml of methyl ethyl ketone and the mixture is heated under reflux for 20 hours with stirring. Thereafter the insoluble constituents are filtered off and the filtrate is concentrated in vacuo. The residue is repeatedly recrystallized from acetone (with, if appropriate, the addition of some methylene chloride to ensure complete dissolution, and gives 11.2 g of brick-red 1-hydroxy-anthraquinone-4-(oxy-2,3-oxido-propane) of melting point 148° C.

Mass spectrum: m/e=296 (M+) (no molar peak for the bis-expoxide according to Example 4—at m/e=352 (M+)).

1H-NMR spectrum (DCCl$_3$): Characteristic signal pattern for:

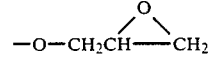

group: δ=2.9 ppm (AB part of an ABX-spectrum, C$\underline{H}_2$—3); δ=3.4 ppm (m, C$\underline{H}$—2); δ=4.3 ppm (AB part of an ABX-spectrum, C$\underline{H}_2$—1).

TLC: R$_F$=0.8 (R$_F$ of starting material: 0.95).

b. If, following the procedure described under Example 3a., a solution of 20 g of 1,4-dihydroxyanthraquinone in 500 ml of methyl ethyl ketone or acetone is boiled for 8 hours under reflux with 20.5 g of potassium carbonate and 50 ml of epibromohydrin, while stirring, and the mixture is then further treated and worked up, a repeated recrystallization from acetone gives the same reaction product, with the same data, as described under Example 3a.

Admittedly, the 1,4-bis-epoxide described in Example 4 can be identified by TLC as a by-product in the crude product first obtained, but it is separated from the desired monoepoxide according to Example 3a. by fractional recrystallization from acetone or by chromatography on neutral aluminum oxide.

| TLC |
| --- |
| (1.) purified product: R$_F$ = 0.8 (no further spots visible) |
| (2.) Crude product: Main spot R$_F$ = 0.8 Subsidiary spot R$_F$ = 0.4 |
| (3.) Starting material R$_F$ = 0.95 |

EXAMPLE 4

Anthraquinone-1,4-bis-(oxy-2,3-oxido-propane)

61.5 g of potassium carbonate and 300 ml of epibromohydrin are added to a solution of 60 g of 1,4-dihydroxyanthraquinone in 150 ml of methyl ethyl ketone and the batch is boiled under reflux for 100 hours, with thorough stirring. It is allowed to cool to room temperature and the insoluble constituents are filtered off. The filtrate is concentrated in vacuo and the resulting oil is caused to crystallize by trituration with about 1 liter of diethyl ether. The crystals are filtered off, rinsed repeatedly with diethyl ether and dried, giving 64 g of dirty yellowish green crystals which in a TLC show only moderate contamination; this product is dissolved in about 200–300 ml of acid-free methylene chloride. The solution is absorbed on a column packed with Woelm, neutral aluminum oxide, activity level II (h=10 cm, 0=8.5 cm). After about 200 ml of first runnings, which are discarded, have been put through, the column is eluted with acid-free methylene chloride until a sample no longer shows any significant contents of reaction product (throughput about 1.5–4 liters of eluant). The eluant is distilled off in vacuo and the crystalline yellow residue is recrystallized from acetone/methylene chloride (the material being dissolved at the boil and the methylene chloride distilled off), with addition of diethyl ether to the solution while still warm. After filtering off the product, washing it with diethyl ether and drying it, about 20 g of anthraquinone-1,4-bis-(oxy-2,3-oxido-propane) of melting point 168° C. are obtained.

1H-NMR spectrum (DCCl$_3$): Characteristic signal pattern for

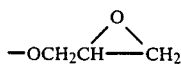

group: δ=2.8 ppm (AB part of an ABX spectrum, C$\underline{H}_2$—3); δ=3.45 ppm (m, C$\underline{H}$—2); δ=4.3 ppm (AB part of an ABX spectrum, C$\underline{H}_2$—1).

Mass spectrum: m/2=352 (M+).

TLC: R$_F$=0.4.

EXAMPLE 5

Anthraquinone-2,6-bis(oxy-2,3-oxido-propane)

a. 40.8 g of potassium carbonate and 200 ml of epibromohydrin are added to a solution of suspension of 40 g of 2,6-dihydroxyanthraquinone in 1,000 ml of butan-2-one and the mixture is heated for 110 hours under reflux, with stirring. The insoluble constituents are filtered off, the filtrate is concentrated in vacuo, the residue is dissolved in methyl ethyl ketone, if appropriate with addition of methylene chloride, the solution is briefly treated with active charcoal and is filtered, and the reaction product is allowed to crystallize out after a part of the solvent has been distilled off. Advantageously, the product is further recrystallized repeatedly from butan-2-one and/or acetone, 5 to 10 g of pale yellow anthraquinone-2,6-bis-(oxy-2,3-oxido-propane) of melting point 188°–191° C. being obtained. This reaction product is at times also obtained during recrystallization in a higher-melting form, namely with melting point 218°–220° C.

b. The filtered-off insoluble constituents obtained above are exhaustively extracted with absolute acetone on a Soxleth extraction vessel. The yellowish green crystals which precipitate after the extractant has cooled are filtered off (about 20 g) and again exhaustively extracted on the Soxleth extraction apparatus, this time using absolute methylene chloride. After the solvent has been distilled off, the residue is recrystallized from acetone or butan-2-one, with addition of methylene chloride. About 10 g of the compound shown in the title, of melting point 218°–220° C., are obtained.

The two forms of the compound shown in the title, namely the low-melting and the high-melting form, show identical IR, NMR and mass spectra and an identical R$_F$ value in a thin layer chromatogram.

Mass spectrum: m/e=352 (M+).

1H-NMR spectrum (in DMSO): Characteristic signal pattern for the

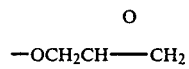

group: δ=2.8 ppm (AB part of an ABX spectrum, C$\underline{H}_2$—1); δ=3.4 ppm (m, C$\underline{H}$—2); δ=4.3 ppm (AB part of an ABX spectrum, C$\underline{H}_2$-13).

TLC: R$_F$=0.78 (R$_F$ of starting material=0.37)

c. In a second batch, in which the reaction is carried out analogously, the reaction mixture is allowed to cool to room temperature after a reaction time of 110 hours, insoluble matter is filtered off and extracted as described under b., with acetone on a Soxleth extraction apparatus, and the crystals which precipitate at 20° C. are isolated and extracted as described under b. on a Soxleth apparatus, but using methylene chloride. Using an isolation technique analogous to that described in b., 24 g of anthraquinone-2,6-bis-(oxy-2,3-oxido-propane) of melting point 219°–222° C. are obtained, the product being completely identical in all spectral data and in the

EXAMPLE 6

Anthraquinone-2,7-bis-(oxy-2,3-oxido-propane)

30.6 g of potassium carbonate and 150 ml of epibromohydrin are added to a solution of 30 g of 2,7-hydroxy-anthraquinone in 700 ml of methyl ethyl ketone and the mixture is heated under reflux for 120 hours, with stirring. It is then filtered (while still hot) through a clarifying layer filter, the filtrate is evaporated in vacuo, and the residue is chromatographed on aluminum oxide, with methylene chloride, as described in Example 4. The product is crystalllized from methyl ethyl ketone, with addition of sufficient methylene chloride to ensure complete dissolution, and 10.8 g of anthraquinone-2,7-bis-(oxy-2,3-oxido-propane) of melting point 208°–212° C. are obtained.

Mass spectrum: m/e=352 (M+).
1H-NMR spectrum: Characteristic signal pattern for the

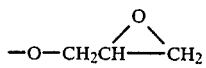

group: $\delta$=2.8 ppm (AB part of an ABX spectrum, C$\underline{H_2}$—3); $\delta$=3.45 ppm (m, C$\underline{H}$—2); $\delta$=4.3 ppm (AB part of an ABX spectrum C$\underline{H_2}$—1).

EXAMPLE 7

Anthraquinone-1,2-(oxy-2,3-oxido-propane)

30.6 g of potassium carbonate and 150 ml of epibromohydrin are added to a solution of 30 g of 1,2-dihydroxyanthraquinone in 700 ml of methyl ethyl ketone and the mixture is heated under reflux for 100 hours, with stirring. It is then filtered (while still hot), the filtrate is concentrated in vacuo and the residue is recrystallized from methyl ethyl ketone, if necessary with addition of sufficient methylene chloride to give complete dissolution. 13.0 g of anthraquinone-1,2-bis-(oxy-2,3-oxido-propane) of melting point 220° C. are obtained.

Mass spectrum: m/e=352 (M+).
1H-NMR spectrum:
Characteristic signal pattern for the

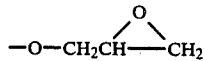

group: $\delta$=2.8 ppm (AB part of an ABX spectrum, C$\underline{H_2}$—3); $\delta$=3.45 ppm (m, C$\underline{H}$—2); $\delta$=4.3 ppm (AB part of an ABX spectrum, C$\underline{H_2}$—1).

EXAMPLE 8

Anthraquinone-1,8-bis-(oxy-2,3-oxido-propane)

30.6 g of potassium carbonate and 150 ml of epibromohydrin are added to a solution of 30 g of 1,8-dihydroxy-anthraquinone in 700 ml of methyl ethyl ketone and the mixture is heated for 100 hours under reflux, with stirring. It is then filtered (while still hot), the filtrate is concentrated in vacuo and the residue is recrystallized from methyl ethyl ketone, if necessary with addition of sufficient methylene chloride to give complete dissolution. 10.5 g of anthraquinone-1,8-bis-(oxy-2,3-oxido-propane) of melting point 187°–189° C. are obtained.

Mass spectrum: m/e=352 (M+).
1H-NMR spectrum: Characteristic signal pattern for the

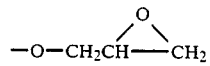

group: $\delta$=2.8 ppm (AB part of an ABX spectrum C$\underline{H_2}$—3); $\delta$=3.45 ppm (m, C$\underline{H}$—2); $\delta$=4.3 ppm (AB part of an ABX spectrum, C$\underline{H_2}$—1).

EXAMPLE 9

Anthraquinone-1,5-bis-(oxy-2,3-oxido-propane)

30.6 g of potassium carbonate and 150 ml of epibromohydrin are added to a solution of 30 g of 1,5-dihydroxy-anthraquinone in 700 ml of methyl ethyl ketone and the mixture is heated for 100 hours under reflux, with stirring. It is then filtered (while still hot), the filtrate is concentrated in vacuo, the residue is chromatographed, if appropriate, on aluminum oxide, in accordance with Example 4, using methylene chloride as the absorption solvent and eluant, the product is crystallized from methyl ethyl ketone, if necessary with addition of sufficient methylene chloride to give complete dissolution, and 11.0 g of anthraquinone-1,5-bis-(oxy-2,3-oxido-propane) of melting point 205° C. are obtained.

Mass spectrum: m/e=352 (M+).
1H-NMR spectrum: Characteristic signal pattern for the

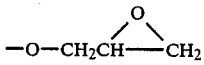

group: $\delta$=2.8 ppm (AB part of an ABX spectrum, C$\underline{H_2}$—3); $\delta$=3.45 ppm (m, C$\underline{H}$—2); $\delta$=4.3 ppm (AB part of an ABX spectrum, C$\underline{H_2}$—1).

EXAMPLE 10

Anthraquinone-6-methoxycarbonyl-1,4-bis-(oxy-2,3-oxido-propane)

3 g of potassium carbonate and 15 ml of epibromohydrin are added to a solution of 3 g of 1,4-dihydroxy-6-methoxycarbonyl-anthraquinone in 70 ml of (absolute) methyl ethyl ketone and the mixture is heated for 100 hours under reflux, with stirring and rigorous exclusion of moisture. The mixture is then filtered (while still hot), the filtrate is concentrated in vacuo and the residue is recrystallized from methyl ethyl ketone, if necessary with addition of sufficient methylene chloride to give complete dissolution, 1.2 g of amorphous anthraquinone-6-methoxycarbonyl-1,4-bis-(oxy-2,3-oxido-propane) being obtained.

Mass spectrum: m/e=410 (M+).
1H-NMR spectrum: Characteristic signal pattern for the

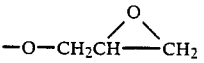

group: δ=2.8 ppm (AB part of an ABX spectrum, C$\underline{H}_2$—3); δ=3.45 ppm (m, C$\underline{H}$—2); δ=4.3 ppm (AB part of an ABX spectrum, C$\underline{H}_2$—1).

EXAMPLE 11

Anthraquinone-3-methyl-1,8-bis-(oxy-2,3-oxido-propane)

3 g of potassium carbonate and 15 ml of epibromohydrin are added to a solution of 3 g of 1,8-dihydroxy-3-methyl-anthraquinone in 70 ml of methyl ethyl ketone and the mixture is heated for 100 hours under reflux, with stirring. It is then filtered (while still hot), the filtrate is concentrated in vacuo and the residue is recrystallized from methyl ethyl ketone, if necessary with addition of sufficient methylene chloride to give complete dissolution, 1.6 g of anthraquinone-3-methyl-1,8-bis-(oxy-2,3-oxido-propane) of melting point 198°–209° C. being obtained.

Mass spectrum: m/e=368 (M+).

1H-NMR spectrum: Characteristic signal pattern for the

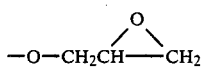

group: δ=2.8 ppm (AB part of an ABX spectrum, C$\underline{H}_2$—3); δ=3.45 ppm (m, C$\underline{H}$—2); δ=4.3 ppm (AB part of an ABX spectrum, C$\underline{H}_2$—1).

EXAMPLE 12

Anthraquinone-5,8-dichloro-1,4-bis-(oxy-2,3-oxido-propane)

3 g of potassium carbonate and 15 ml of epibromohydrin are added to a solution of 3 g of 1,4-dihydroxy-5,8-dichloro-anthraquinone in 70 ml of methyl ethyl ketone and the mixture is heated for 100 hours under reflux, with stirring. It is then filtered (while still hot), the filtrate is concentrated in vacuo and the residue is recrystallized from methyl ethyl ketone, if necessary with addition of sufficient methylene chloride to give complete dissolution, 1.1 g of anthraquinone-5,8-dichloro-1,4-bis-(oxy-2,3-oxido-propane) of melting point 201°–212° C. being obtained.

Mass spectrum: m/e=421 (M+).

1H-NMR spectrum: Characteristic signal pattern for the

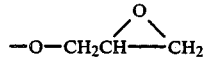

group: δ=2.8 ppm (AB part of an ABX spectrum, C$\underline{H}_2$—3); δ=3.45 ppm (m, C$\underline{H}$—2); δ=4.3 ppm (AB part of an ABX spectrum, C$\underline{H}_2$—1).

EXAMPLE 13

Anthraquinone-2-acetoxy-1,4-bis-(oxy-2,3-oxido-propane)

3 g of potassium carbonate and 15 ml of epibromohydrin are added to a solution of 3 g of 1,4-dihydroxy-2-acetoxy-anthraquinone in 70 ml of methyl ethyl ketone and the mixture is heated for 100 hours under reflux, with stirring. It is then filtered (while still hot), the filtrate is concentrated in vacuo and the residue is recrystallized from methyl ethyl ketone, if necessary with addition of sufficient methylene chloride to give complete dissolution, 1.0 g of amorphous anthraquinone-2-acetoxy-1,4-bis-(oxy-2,3-oxido-propane) being obtained.

Mass spectrum: m/e=410 (M+).

1H-NMR spectrum: Characteristic signal pattern for the

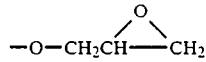

group: δ=2.8 ppm (AB part of an ABX spectrum, C$\underline{H}_2$—3); δ=3.45 ppm (m, C$\underline{H}$—2); δ=4.3 ppm (AB part of an ABX spectrum, C$\underline{H}_2$—1).

EXAMPLE 14

Anthraquinone-5-nitro-1,4-bis-(oxy-2,3-oxido-propane)

3 g of potassium carbonate and 15 ml of epibromohydrin are added to a solution of 3 g of 1,4-dihydroxy-5-nitro-anthraquinone in 70 ml of methyl ethyl ketone and the mixture is heated for 100 hours under reflux, with stirring. It is then filtered (while still hot), the filtrate is concentrated in vacuo and the residue is recrystallized from methyl ethyl ketone, if necessary with addition of sufficient methylene chloride to give complete dissolution, 1 g of anthraquinone-5-nitro-1,4-bis-(oxy-2,3-oxido-propane) of melting point 171°–182° C. being obtained.

Mass spectrum: m/e=401 (M+).

1H-NMR spectrum: Characteristic signal pattern for the

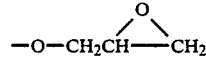

group: δ=2.8 ppm (AB part of an ABX spectrum, C$\underline{H}_2$—3); δ=3.45 ppm (m, C$\underline{H}$—2); δ=4.3 ppm (AB part of an ABX spectrum, C$\underline{H}_2$—1).

EXAMPLE 15

Anthraquinone-3-methoxy-1,8-bis-(oxy-2,3-oxido-propane)

3 g of potassium carbonate and 15 ml of epibromohydrin are added to a solution of 3 g of 1,8-dihydroxy-3-methoxy-anthraquinone in 70 ml of methyl ethyl ketone and the mixture is heated for 100 hours under reflux, with stirring. It is then filtered (while still hot), the filtrate is concentrated in vacuo and the residue is recrystallized from methyl ethyl ketone, if necessary with addition of sufficient methylene chloride to give complete dissolution, 1.0 g of anthraquinone-3-methoxy-1,8-bis-(oxy-2,3-oxido-propane) of melting point 160°–185° C. being obtained (ill-defined).

Mass spectrum: m/e=382 (M+).

1H-NMR spectrum: Characteristic signal pattern for the

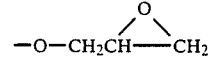

group: δ=2.8 ppm (AB part of an ABX spectrum, C$\underline{H}_2$—3); δ=3.45 ppm (m, C$\underline{H}$—2); δ=4.3 ppm (AB part of an ABX spectrum, C$\underline{H}_2$—1).

EXAMPLE 16

Anthraquinone-hydroxy-bis-(oxy-2,3-oxido-propane)

6.15 g of potassium carbonate and 30 ml of epibromohydrin are added to a solution of 6 g of 1,4,6-trihydroxy-anthraquinone in 150 ml of methyl ethyl ketone and the mixture is boiled under reflux, with thorough stirring, until a sample taken shows a distinct molecular weight peak in the mass spectrum at m/e≃368 (M+). The higher molecular mass spectrum peaks≧368 should be comparatively small. The reaction time for this is as a rule 2 to 4 days.

The mixture is allowed to cool to room temperature and the insoluble constituents are filtered off. The filtrate is concentrated in vacuo and the resulting oil is caused to crystallize by titration with about 20 ml of diethyl ether. The product is filtered off, the crystals are repeatedly rinsed with diethyl ether and dried, and 10 g of dirty red crystals are obtained; these are repeatedly recrystallized from methylene chloride/acetone/diethyl ether. Yield: 2.9 g of a reddish product of melting point 198°–214° C. (very ill-defined due to the presence of a mixture of isomers of anthraquinone-hydroxy-bis-(oxy-2,3-oxido-propane)).

1H-NMR spectrum (DCCl$_3$): Characteristic signal pattern for the

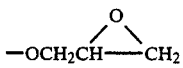

group: δ=2.8 ppm (AB part of an ABX spectrum, CH$_2$—3); δ=3.45 ppm (m, CH—2); δ=4.3 ppm (AB part of an ABX spectrum, CH$_2$—1).

Mass spectrum: m/e=368 (M+).

EXAMPLE 17

Anthraquinone-dihydroxy-bis-(oxy-2,3-oxido-propane)

6.15 g of potassium carbonate and 30 ml of epibromohydrin are added to a solution of 6 g of 1,4,5,8-tetrahydroxy-anthraquinone in 150 ml of methyl ethyl ketone and the mixture is boiled under reflux, with thorough stirring, until a sample taken shows a distinct molecular weight peak in the mass spectrum at m/e=384 (M+). The higher molecular mass spectrum peaks≧384 should be comparatively small. The reaction time for this is as a rule 3 to 5 days.

The mixture is allowed to cool to room temperature and the insoluble constituents are filtered off. The filtrate is concentrated in vacuo and the resulting oil is caused to crystallize by titration with about 20 ml of diethyl ether. The product is filtered off, the crystals are repeatedly rinsed with diethyl ether and dried, and 11 g of dirty red crystals are obtained; these are repeatedly recrystallized from methylene chloride/acetone/diethyl ether. Yield: 2.4 g of a reddish product of melting point 194°–212° C. (very ill-defined due to the presence of a mixture of isomers of anthraquinone-dihydroxy-bis-(oxy-2,3-oxido-propane)).

1H-NMR spectrum (DCCl$_3$): Characteristic signal pattern for the

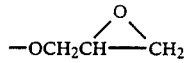

group: δ=2.8 ppm (AB part of an ABX spectrum, CH$_2$—3); δ=3.45 ppm (m, CH—2); δ=4.3 ppm (AB part of an ABX spectrum, CH$_2$—1).

Mass spectrum: m/e=348 (M+).

We claim:

1. A compound of the formula I

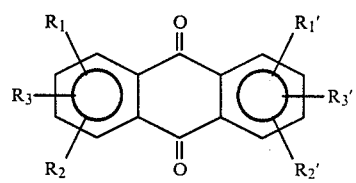

where R$_1$ and R$_1$' are identical or different and are hydrogen, hydroxyl or the radical

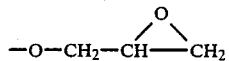

R$_2$ and R$_2$' are identical or different and are hydrogen or one or more hydroxyl, C$_1$–C$_4$-alkyl, C$_1$–C$_4$-alkoxy, C$_1$–C$_4$-alkoxycarbonyl, C$_1$–C$_4$-alkanoyloxy, aryloxy, Ar—C$_1$–C$_4$-alkoxy, nitro groups or halogen atoms, and R$_3$ and R$_3$' are different and are hydrogen or the radical

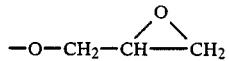

2. 1-Hydroxy-anthraquinone-4-(oxy-2,3-oxido-propane).
3. Anthraquinone-1,4-bis-(oxy-2,3-oxido-propane).
4. Anthraquinone-2,6-bis-(oxy-2,3-oxido-propane).
5. Anthraquinone-1,8-bis-(oxy-2,3-oxido-propane).
6. A pharmaceutical composition comprising an effective amount of a compound of the formula I as recited in claim 1.

* * * * *